United States Patent [19]

Zarling et al.

[11] Patent Number: 5,223,414
[45] Date of Patent: Jun. 29, 1993

[54] PROCESS FOR NUCLEIC ACID HYBRIDIZATION AND AMPLIFICATION

[75] Inventors: David A. Zarling, Menlo Park; Elissa P. Sena, Palo Alto; Christopher J. Green, Novato, all of Calif.

[73] Assignee: SRI International, Menlo Park, Calif.

[21] Appl. No.: 520,321

[22] Filed: May 7, 1990

[51] Int. Cl.⁵ .............................................. C12P 19/34
[52] U.S. Cl. ......................................... 435/91; 435/6; 935/77; 935/78
[58] Field of Search ........................... 435/6, 91, 172.3; 935/78, 77; 436/501; 530/825

[56] References Cited

U.S. PATENT DOCUMENTS 4,683,195  7/1987  Mullis et al.
4,683,202  7/1987  Mullis.
4,713,337  12/1987 Jasin et al.
4,888,274  12/1989 Radding et al.

OTHER PUBLICATIONS

Griffith et al., Biotechnology Abstracts, DBA Accession No. 89-13540, (1989).
Scharf, S. J., et al., Science 233, p1076 (1986).
Madiraju, M. V. V. S., et al., Proc. Natl. Acad. Sci. USA 85, p6592 (1988).
Radding, C. M., Ann. Rev. of Genetics 16, p405 (1982).
Roman, L. J., et al., Biochemistry 25, p7375 (1986).
Kowalczykowski, S. C., et al., J. Mol. Biol. 193 p81 (1987).
Kowalczykowski, S. C., et al., Proc. Natl. Acad. Sci. USA 84, p3127 (1987).

Primary Examiner—Amelia Burgess Yarbrough
Attorney, Agent, or Firm—Peter J. Dehlinger

[57] ABSTRACT

The present invention is directed to a method of achieving RecA protein facilitated amplification of a double-stranded DNA target sequence having first and second complementary strands, each strand with 5' and 3' ends. The method involves complexing a primer complementary to a 5' end region of the first strand and a primer complementary to a 5' end region of the second strand with RecA protein in the presence of ATP-γ-S. The complexed primers are then reacted in a mixture also containing the target sequence, all four dNTPs, RecA protein and DNA polymerase. The reaction is conducted below the temperature required for thermal dissociation of the two target strands and continued until a desired degree of amplification of the target sequence is achieved.

The present invention further includes the cloning and identification of the coding sequences for the RecA protein of *Thermus aquaticus*.

4 Claims, 7 Drawing Sheets

FIG.13

```
TTCCCTCTCGTTCGTGTACGGTATTCCTCATTGCGGAACCGCCGGTTCGGGATAGATGAAGGGAACGG        -42
CCATGTCTCAGGCTGCATTGCGTCTCGTGGACAAGGATACCATGGATAGACAGAAGGCTTTGGAAGCTGC       29
CGTCAGCCAGATCGAGCGGGCATTCGGCGAAGGCTCCATCATGAAGCTGGGCGGCAAGGATCAGGTGGTC       99
GAGACCGAAGTGGTCTCCACCCGGATCCTGGGCCTTGATGTGGCGCTCGGCATCGGCGGCGTTCCGCGCG      128
GCCGTATCATCGAGGTCTATGCCCCGGAAAGCTCGGCAAGACCACCCTGGCGCTGCACATCATCGCCGA       198
GGCGCAGAAGAAGGCGCACCTGCGCCTTCGTCGATGCCGAACACGCGCTTGACCCCTCCTATGCCCGT       268
AAGCTGGGCGCGCTGGAAGACGAGCTGCTGATCAGCGAGCCCGACGCGCTGGCGAGCAGGCCCTGAAATCGCCG   338
ACACCCTGGTACGCCCCGGCCGTGGACGTTCTGGTGGTGATTCGGTGGCCGCATTGGTGCCCCGCGG        408
CGAGCTGGAAGGCGAGATGGGCGACAACCATATGGGCCTGCACGCCCGCCTGATGAGCCAGGCGCTGCGC       478
AAGCTGACCGGTTCGGTTATCCAAGTTCCAAAAACCATCGTCATCTTCATCAACCAGATCCGCATGAAGATCG   548
GCGTGATGTTCGGCAATCCCGGGCGCCATCAAGGACAGGAGACGAGGTCGTGGGCAACCAGACCCGCTCAAGGTG  618
GGAGATCCGCCCGGGTCGGCGGCCATCAAGGACAGGAGGACGAGGTCGTGGGCAACCAGACCCGCTCAAGGTG   688
GTGAAGAACAAGCTGGCTCCGCCGTTCAAGGTGGTGGACTTCGACATCATGTATGCGAAGGCATCTCCA       758
AGATGGGTGAGCTCATCGATCGGGCGTCAAGGCCAATGTGGTGAAGAAATCGGGGCCTGGTTCTCCTA        828
CAACTCCACCCGCATCGGCCAGGCCGCGAGAACGCCAAGCAGTTCCTGCGCGACAATCCGGCCATGGCC       898
GCCGAGATCGAAGGCCATCCGCCAGAATGCCGCCTCATCTCCGAGGCCCTGCCGCCGGTCCCGGACC        968
TGGACGGCACGCCGGGTCGCGCGAATAACCCCTCGCCGCGGTGCCGAAAACCACAGGCCACCCGGCAACAC      1038
```

PROCESS FOR NUCLEIC ACID HYBRIDIZATION AND AMPLIFICATION

FIELD OF THE INVENTION

The present invention relates to methods for using RecA protein(s) to catalyze DNA synthesis, repair and amplification reactions.

REFERENCES

Blaho, J. A., et al., J. Biol. Chem., 262, p. 6082, (1987).
Cheng, S., et al., J. Biol. Chem. 263, p. 15110 (1988).
Collins, M., et. al., in: "DNA Probes—Applications in Genetic and Infectious Disease and Cancer," (L.S. Lerman, Ed.), Cold Spring Harbor Laboratory, p 137-141 (1986).
Cox, M. M., et al., Ann. Rev. Biochem. 56, p. 229 (1987).
Fuchs, R. P. P., et. al., Biochem. 11, p. 2659 (1972).
Fuchs, R. P. P., et al., Biochem., 15, p. 3347, (1976).
Green, C.J., et al., B S Nucl. Acids Res. II, p. 5763-5774 (1983).
Hingerty, B. E., et al., J. of Biomolecular Structure and Dynamics, 4, p. 365, (1986).
Kriek, E., Cancer Res., 32, p. 2042, (1972).
Leahy, M. C., et al., J. Biol. Chem., 261, p. 6954-6960 (1986).
Lu, C., et al., Proc. Natl. Acad. Sci., USA, 83, p 619, (1986).
McConlogue, L., et al, Nucleic Acids Res. 16, p. 9869 (1988).
Madiraju, M. V. V. S., et. al., Proc. Natl. Acad. Sci. (USA) 85, p. 6592 (1988).
Maniatis, T., et. al., *Molecular Cloning: A laboratory Manual*, Cold Spring Harbor Lab., Cold Spring Harbor, NY (1982).
Mullis, K. B., et al., U.S. Pat. No. 4,683,195 (1987).
Mullis, K. B., U.S. Pat. No. 4,683,202 (1987).
Radding, C. M., Ann. Rev. Genet. 16, p. 405 (1982).
Rigas, B., et al., Proc. Natl. Acad. Sci. USA, 83, p. 9591-9595 (1986).
Sage, E. et al., Proc. Natl. Acad. Sci., USA, 77, p. 4597, (1980).
Sage, E., et al., Nucleic Acid Res., 9, p. 1241, (1981).
Santella, R. M., et al., Nucleic Acid Res., 9, p. 5459, (1981a).
Santella, R. M., et al., Proc. Natl. Acad. Sci., USA, 78, p. 1451, (1981b).
Saiki, R. K., et al., Science 239, p. 487 (1988).
Shi, Y-B., et al., Nucleic Acid Res., 16, p. 8945; (1988).
Silberklang, M., et. al., Methods in Enzymol. 59, p. 58 (1979).
Shuldiner, A. R., et al., Nucleic Acid Res. 17, p. 4409 (1989).
Wells, R. D., et al., Biol. Chem., 257, p. 10166, (1982).
Zarling, D. A., et. al., J. Molec. Biol. 176, p. 369 (1984a).
Zarling, D. A., et. al., J. Biolmol. Struct. Dynam. 1, p. 1081 (1984b).
Zarling, D.A., et al., J. Molec. Biol. 211, p. 147 (1990).

BACKGROUND OF THE INVENTION

RecA+ protein (wild type) is a 38,000 dalton protein found in the bacterium *Escherichia coli*, which is important for homologous DNA recombination. Most information about its biochemistry and enzymology comes from studies on purified RecA+ protein. Numerous in vitro studies have shown that RecA+ protein is intimately involved in the pairing reaction between homologous DNA sequences that ultimately leads to homologous recombination events (see Cox et. al. for a recent review of RecA+ protein properties). It is this pairing reaction that makes RecA+ protein highly useful for DNA diagnostics and therapeutics applications.

In the presence of ATP, RecA+ protein catalyzes strand exchange between a number of substrates, the most relevant for DNA probe applications being single- and double-stranded DNAs. Single-stranded DNA (probe) interacts with the homologous portion of the double-stranded ("native") target sequences, initially by forming a recombination intermediate containing hybridized, partially joined molecules. This is followed by branch migration, and forming of fully hybrid molecules between the original single- and double-stranded DNAs, depending upon the extent of their homology. This reaction results in a product that is a hybrid between probe and target. Such hybrids can be easily detected using, for example, radio-labeled, enzyme-labeled, chemiluminescently-labeled, phosphorescently-labeled or fluorescently-labeled probes.

The present application demonstrates the feasibility of using RecA+ protein to facilitate and improve the efficiency of hybridization reactions involving single-stranded primer and complementary native double-stranded target sequences. In particular, RecA+ protein is particularly well suited for many DNA probe applications because the double-stranded target DNA does not need to be denatured (e.g., by heating) before hybridization. Further, RecA+ protein is useful in facilitating the initiation and completion of DNA chain elongation at DNA sequences that are either damaged or difficult to denature.

SUMMARY OF THE INVENTION

It is one object of the present invention to provide a method of achieving RecA protein facilitated amplification of a double-stranded DNA target sequence having first and second complementary circular or linear strands, each linear strand with 5° and 3'0 ends. The method involves complexing a primer complementary to a 5' end region of the first strand and a primer complementary to a 5' end region of the second strand with RecA protein in the presence of ATP-γ-S. The complexed primers are then reacted in a mixture also containing the target sequence, all four dNTPs, RecA protein and DNA polymerase. The reaction is conducted below the temperature required for thermal dissociation of the two target strands and continued until a desired degree of amplification of the target sequence is achieved.

The method of the present invention is particularly useful when the target DNA has inhibitory secondary structure or otherwise amplification resistant regions.

During the course of the DNA synthesis reaction further additions of DNA polymerase, RecA protein, and/or ATP-γ-S may be made.

One embodiment of the present method includes that the two primers are complementary to the same DNA sequence. Another embodiment includes the use of primers containing terminal 5' sequences which are non-complementary to the DNA target sequence. These non-complementary sequences may include sequences coding for restriction endonuclease recognition sites, capture sequences, reporter sequences, RecA protein loading sequences, Z-DNA sequences or double-stranded tails.

An important advantage of the invention is use of the method for the synthesis/amplification of physically or chemically damaged DNA substrates.

A preferred embodiment of the invention includes that the RecA protein is the protein product of the recA-803 gene.

The method of the present invention can also be used to achieve synthesis or amplification of DNA by conducting the DNA synthesis reactions at a constant temperature above about 50° C. and below the temperature required for thermal dissociation of the target strands and their respective primers. In this embodiment useful forms of the RecA protein and DNA polymerase can be obtained from Thermus aquaticus.

The present invention further includes the cloning and identification of the coding sequences for the RecA protein of Thermus aquaticus.

The RecA coated primers of the present invention also serve as useful probes in hybridization-based diagnostic systems because of their enhanced ability to locate and pair with complementary sequences and sequences in regions of normally inhibitory secondary structure.

BRIEF DESCRIPTION OF THE DRAWINGS

FIG. 13 shows the partial sequence of the RecA gene of *Aquaspirillum magnetotacticum*.

DETAILED DESCRIPTION OF THE INVENTION

I. Comparison of the DNA Binding and DNA Strand-transfer Activities of RecA+ and RecA-803 Protein One focus of the present invention is to provide superior RecA+ protein catalysts to facilitate DNA hybridization and DNA synthesis reactions. Experiments performed in support of the present invention suggested recA-803 protein to be a valuable candidate for such a catalyst. The recA-803 mutant gene has been cloned and sequenced, and the protein product over-expressed and purified (Madiraju et. al.). This new recA mutant protein more efficiently forms more stable recombination intermediates between target and probe DNAs than wild-type RecA+ protein as judged by nitrocellulose filter binding assays (Madiraju et. al.). This observation suggests that the DNA pairing efficiency of the recA-803 protein, as measured by a nitrocellulose filter binding assay, is significantly greater than that of the wild-type RecA+ protein. Under certain conditions, the mutant recA protein catalyzes the pairing reaction with faster kinetics and to a greater final yield than is usually achieved by the wild-type RecA+ enzyme.

Large quantities of mutant recA-803 protein have been isolated from E. coli containing a plasmid (Dr. A. John Clark, Dept. Mol. Biology (UC Berkeley) that over-expresses the gene; approximately 40% of the total protein in the bacterial cell is mutant recA-803 protein.

Figure 1:
FIG. 1 shows the results of the electrophoretic separation of DNA binding reactions comparing the activities of RecA+ and recA-803 proteins.

Example 1 (FIG. 1) presents gel retardation assay data to examine the relative DNA binding efficiencies of RecA+ and recA-803 proteins. RecA+ or recA-803 protein is reacted with the double-stranded linearized DNA of phiX174 under conditions allowing formation of protein/DNA complexes. The reactions were split into two samples; half of each sample was treated with a detergent, such as SDS, to destroy the protein/DNA complexes. The treated and untreated samples were run side-by-side on 0.7% agarose gels (see Materials and Methods). A basis of the gel retardation assay is that DNA/protein complexes migrate much more slowly through the matrix of a gel. FIG. 1, lanes 7 and 8, illustrate untreated and treated samples, respectively. Comparison of lanes 3 (RecA+ protein) and 7 (recA-803 protein) clearly illustrates that, in comparison to RecA+ protein, recA-803 protein binds much more efficiently to doublestranded linear phiX-174 DNA; similar experiments with double-stranded plasmid or viral DNAs gave identical results.

Figure 2B:
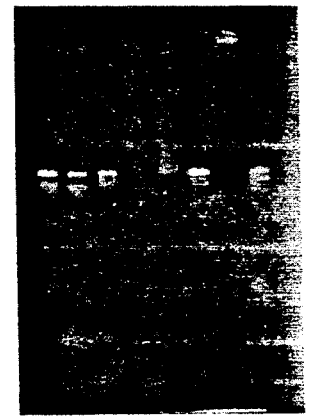
FIG. 2B shows the results of strand-transfer reactions comparing the activities of RecA+ and recA-803 proteins.
Figure 2A:
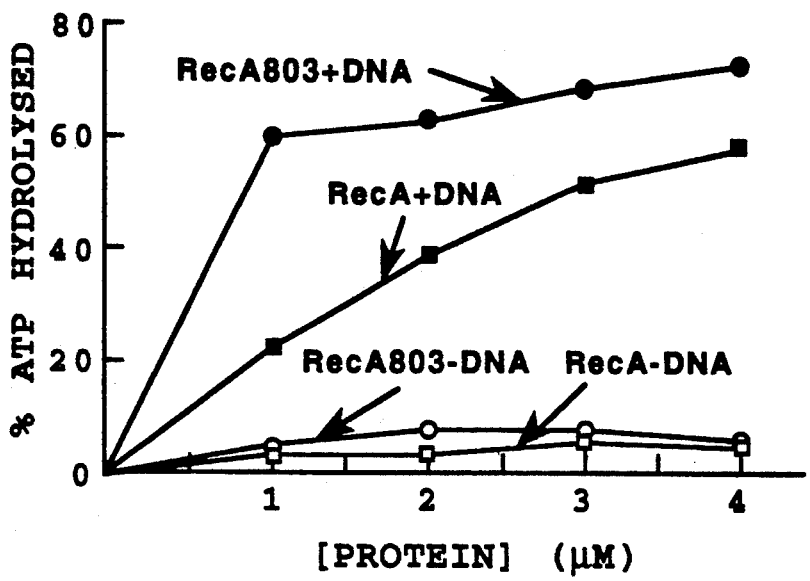
FIG. 2A shows the results of ATP hydrolysis reactions comparing the ATPase activity of RecA+ and recA-803 proteins.

Example 2 presents data showing that recA-803 protein is also a superior catalyst in comparison to RecA+ protein, in hydrolysis of ATP and in producing significantly greater amounts of DNA strand transfer products. In the experiment described in Example 2A, it is clear that the recA-803 protein exhibits significantly more DNA dependent ATPase activity than the RecA+ protein (FIG. 2A). In Example 2B single-stranded phiX-174 virion circular DNA was preincubated with recA-803 or RecA+ protein proteins for 10 minutes at 37° C. to form a Radding-type filament (Radding). The double-stranded target was then added and the strands were transferred with ATPγS as a cofactor. These results demonstrate that recA-803 catalyzes a significantly greater amount of strand-transfer product in comparison to RecA+ protein. The strand-transfer products appear as a discrete band indicated by the arrow in FIG. 2B. Comparison of lanes 3 and 6 (RecA+ protein) to lane 8 (recA-803 protein) illustrates recA-803 protein's increased efficiency in generating DNA strand transfer products. From this and similar experiments the recA-803 protein appears to produce about 5-7 fold more Form II strand-transfer products than RecA+ protein.

The properties of increased ability to bind DNA and increased efficiency in the catalysis of the strand-transfer reaction make recA-803 protein a superior catalyst for DNA synthesis, hybridization, diagnostics and therapeutics applications. These desirable properties make recA-803 protein an ideal catalyst to provide rapid and efficient assays for hybridizing DNA probe sequences with native double-stranded DNA targets in solution. Such assays can make use of any separation system (Collins et. al., Rigas et. al., Leahy et. al.) that differentiates between non-hybridized probe (which remains single-stranded) and hybridized probe target complex (which is partially duplex or multi-stranded, i.e., containing double-stranded regions with portions of single-stranded probe attached).

The use of RecA protein catalyzed enhanced hybridization with homologous sequences in DNA diagnostics eliminates all the necessary laborious steps involved in the usual denaturation of the target DNA and overcomes the serious limitations posed by "snap-back" and other repetitive sequences, which appear unamenable to denaturation and, therefore, detection. In nature, functions of RecA+ protein most likely include facilitating DNA polymerization or recombination through (i) regions of complex or unusual secondary structure, or (ii) chemically or physically damaged DNA sequences.

II. RecA Protein's Enhanced Binding to Damaged DNA or DNA having the Z Conformation E. coli RecA+ protein is a major participant in the recognition and subsequent repair of damaged DNA double-helices. Certain physical and chemical agents, such as UV light (Lu et. al.) and psoralen (Shi et. al.), which can adduct and/or distort pyrimidine bases in double-stranded DNA conformation, are known to increase RecA+ protein binding. RecA+ protein recognition of purine-adducted double-helical DNA has not been examined previously. N-acetoxy-N-2-acetylaminofluorene (N-AcO-AAF) is a potent mutagen and model chemical carcinogen that covalently binds deoxyguanine residues yielding adducts primarily at the C-8 position (Kriek). This modification causes extensive topological changes and unwinding of the DNA helix by inducing the rotation of the deoxyguanine base from the anti to the syn conformation (Fuchs et. al., 1976). Energy minimization studies suggest that this rotation may be accompanied by insertion of the heterocyclic adduct into the helix interior causing a bend in the helical axis (Hingerty et. al.). Furthermore, covalent modification with N-AcO-AAF induces a B→Z transition in duplex DNA of certain alternating purine-pyrimidine or other sequences (Sage et. al., 1980, 1981; Santella et. al., 1981a, 1981b; and Wells et. al.).

Figure 3:
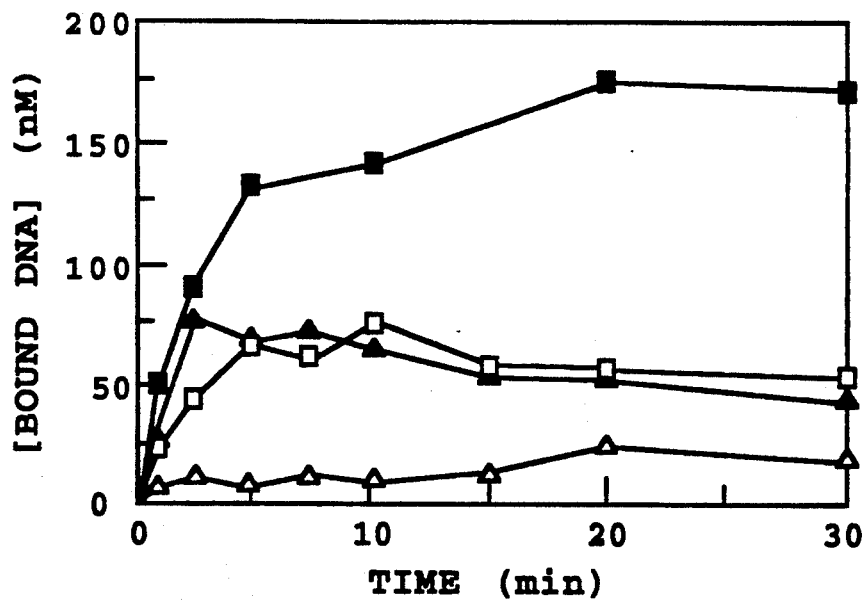
FIGS. 3, 4A and 4B show the results of RecA+ protein/-double-stranded DNA binding assays.

Example 3 describes the results of RecA+ protein/double-stranded DNA binding assays. Blaho et. al. have previously shown that RecA+ protein preferentially binds to brominated or methylated linear synthetic Z-DNA compared with the B-DNA polymers. The results of Example 3, presented in FIG. 3, illustrate a preferential binding to the brominated substrate, consistent with the results of Blaho et. al. Further, the results in FIG. 3 show that RecA+ binding to the duplex synthetic DNA at neutral pH with ATP$\gamma$S as a cofactor is enhanced by purine adduction with N-AcO-AAF. In these and other similar experiments, increased N-AcO-AAF adducts in the duplex DNA increased RecA+ protein binding to the DNA duplex. Binding was proportional to the degree of N-AcO-AAF adduction in the range of 5-20% N-AcO-AAF adduction.

The results in Example 4 (FIGS. 4A and 4B) clearly illustrate RecA+ protein apparent sequence-specificity in preferential binding affinities to the double-stranded oligo-[d(C-A)•d(G-T)] relative to the duplexes generated from oligo-[d(br$^5$C-G)] or oligo-[d(C-G)]. RecA+ protein shows sequence (FIGS. 4A and 4B) and conformation (FIG. 3) specific binding preferences for these DNA duplexes.

RecA protein, accordingly, has valuable diagnostic and therapeutic applications. If the target DNA has been damaged or has unusual secondary structure, traditional methods of DNA hybridization and/or synthesis may be ineffectual. The results of the experiments presented in Examples 3 and 4 illustrate the value of using RecA protein's ability to promote binding to complex DNA and complementary base pairing.

III. Enhancement of In Vitro DNA Synthesis by RecA+ and recA-803

Prior art DNA amplification methods are all based on a three-step process involving DNA template denaturation, primer hybridization, and primer extension by DNA polymerase (Mullis, and Mullis et al.); the present invention provides unique and valuable alternatives, utilizing RecA protein catalysis.

One new method of RecA protein catalyzed DNA amplification involves incubating DNA target sequences and DNA primers complementary to the target sequence with RecA+ protein or recA-803 protein in the presence of ATP or ATP$\gamma$S at 37° C. These conditions permit RecA-protein-catalyzed Radding-type D-loops or joint molecules between the primers and the target DNA. These stable RecA-catalyzed joint molecules are elongated with the Klenow fragment of DNA polymerase I.

Figure 5:
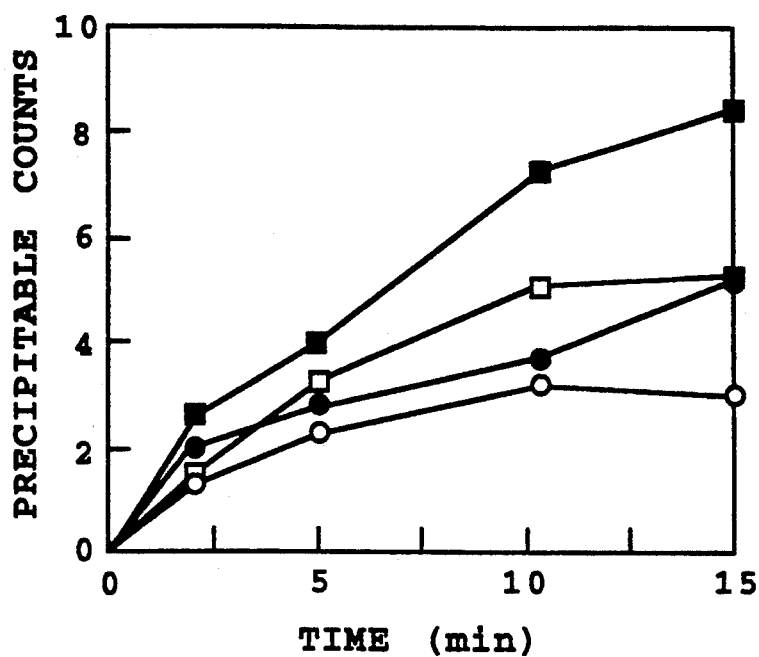
FIG. 5 illustrates the effects of RecA+ protein and single-strand binding protein on bulk DNA synthesis from single-stranded DNA templates.

Example 5 describes the enhancing effect of RecA+ protein on DNA synthesis directed from a single-stranded template. The data presented in FIG. 5 shows the enhancement of single-stranded DNA synthesis by RecA+ and E. coli single-strand binding (SSB) proteins; the two proteins appear to have a synergistic effect. Synthesis on phiX-174 single-stranded circular DNA templates was enhanced by coating the primers with RecA+, thus generating a Raddingtype filament. Inclusion of E. coli SSB protein in the reaction also enhanced single-stranded DNA directed DNA synthesis as measured by incorporation of [$^3$H]dGTP into high-molecular-weight (cold TCA insoluble) DNA.

Figure 6:
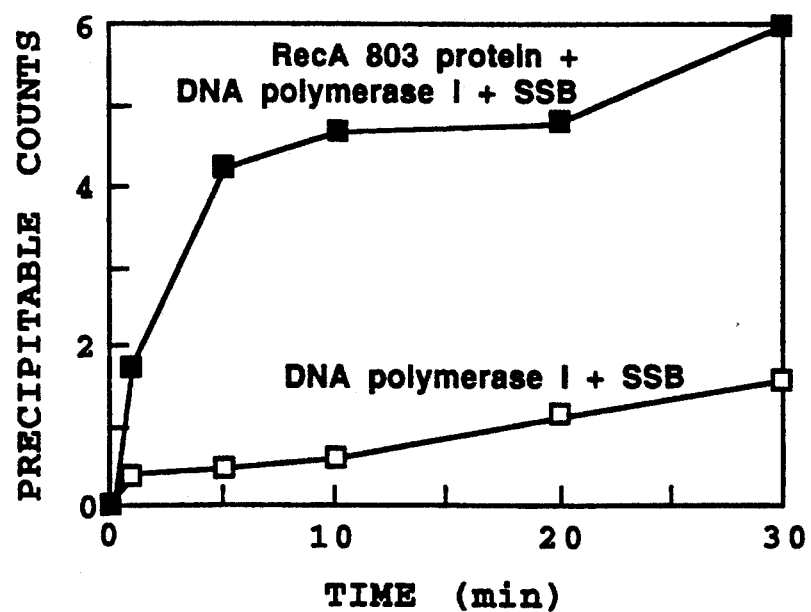
FIG. 6 illustrates the effect of recA-803 protein on bulk DNA synthesis from double-stranded linear templates.

The effect of RecA protein on DNA synthesis from a double-stranded DNA (dsDNA) template was also examined (Example 6). The data presented in FIG. 6 shows recA-803 protein-enhanced DNA synthesis from a double-stranded template using 18-mer primers. The primers were reacted with recA-803 protein (3 $\mu$M) for 5 minutes at 37° C. to form filaments before addition of the dsDNA. Following an additional 5-minute incubation, Klenow large fragment of E. coli DNA polymerase I was added. RecA-803 protein significantly enhanced DNA synthesis as judged by increased incorporation of [α-$^{35}$S]dATP into high-molecular-weight DNA.

Examples 5 and 6 show that the rates and extent of DNA synthesis can be significantly enhanced by primers coated with RecA+ or recA-803.

Figure 7:
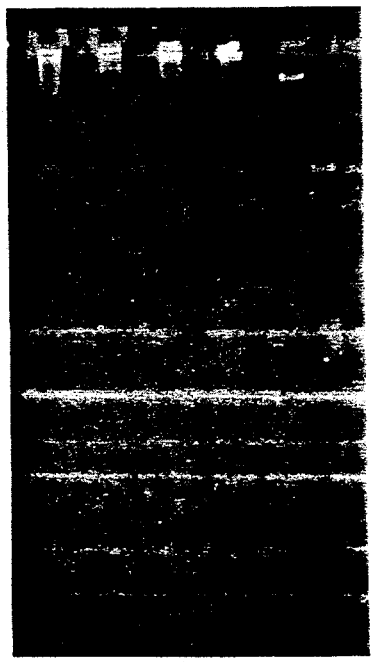
FIG. 7 shows the results demonstrating the RecA+ protein enhancement of DNA synthesis from native lambda DNA templates.

Example 7 demonstrates that RecA protein is able to enhance DNA synthesis from native lambda viral DNA templates. In Example 7 the reactions were assembled at room temperature without the primers. RecA+ protein was incubated with the two 25-mer single-stranded primers (PCR01 and PCR02, Table 1). Next, ATP-γ-S and SSB protein were added to the reaction, followed by the native λ DNA template. Reactions were incubated in a 37° C. heat block and equilibrated at 37° C. for 3 minutes prior to the addition of Klenow DNA polymerase. Following the initiation of the reaction by the first addition of Klenow, subsequently, at ten-minute intervals over the 80 minute time course, an additional 1.0 unit of fresh Klenow polymerase was added. Reactions were sampled and the amount of newly synthesized DNA was measured. The data presented in FIG. 7 shows that native λ DNA synthesis is enhanced by including RecA+ protein and ATPγS in long-term (72-hour) reactions catalyzed by Klenow DNA polymerase at a single temperature, 37° C. The enhancement of DNA synthesis is evidenced by enhanced ethidium bromide binding and staining of DNA products separated by electrophoresis on 0.7% agarose gels.

Figure 8:
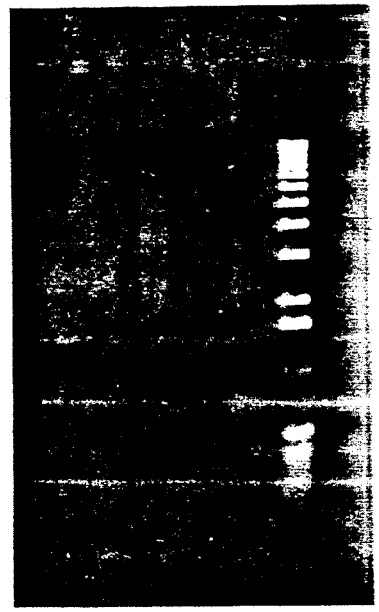
FIG. 8 shows the results demonstrating that the enhancement of DNA synthesis by RecA+ protein does not depend on the presence of single-strand binding protein.

Example 7 presents data showing that the ability of RecA protein to enhance DNA synthesis on dsDNA templates is not dependent on the presence of SSB protein. The data presented in FIG. 8 shows DNA synthesis in the absence of SSB protein (lane 1) and further demonstrates RecA+ protein's ability to enhance DNA synthesis in short term reactions (8 successive additions of polymerase every 10 minutes for 80 minutes).

Figure 9:
FIG. 9 shows the results demonstrating the dependence of RecA+ protein catalyzed DNA synthesis on the presence of specific primers.

The primer dependent nature of the RecA protein catalyzed DNA synthesis is described in Example 8. The data presented in FIG. 9 shows enhanced native DNA synthesis in polymerase reactions with exonuclease free (US Biochemicals) double mutants of the Klenow large fragment of *E. coli* DNA polymerase I only in the presence of RecA+ protein and primers.

A 500-bp DNA template was enzymatically synthesized (Amplitag$^R$ kit, Perkin-Elmer-Cetus) using PCR01 and PCR02 primer pairs (Table 1). This double-stranded product was used as a simple 500-bp template with 40-mer primers PCR01 and PCR02 (Table 1) for DNA synthesis reactions. The reactions were incubated for 17.5 hours at 37° C. using exonuclease-free double mutants of the Klenow large fragment of *E. coli* DNA polymerase I. The data presented in FIG. 10 (Example 9) (lane 4) shows a band of newly synthesized DNA products with an electrophoretic mobility and molecular weight matching the 500-bp native λ DNA template. The synthesis of these DNA products was absolutely dependent on the addition of RecA+ protein to the reaction. Under the same conditions, reactions supplemented with both RecA+ protein and SSB proteins produced other lower-molecular-weight products (lane 5). This result suggested that the DNA synthesis product is more heterogeneous when SSB protein is present; that is, the protein is having a negative effect in terms of specificity although bulk DNA synthesis may be improved in the presence of SSB protein.

In another experiment, 500-bp DNA products were synthesized from 500-bp λ DNA templates with the 25-mer primer pairs (Example 9). Table 2, presented in Example 9, summarizes a number of reaction conditions under which the RecA+ protein's ability to catalyze DNA synthesis has been tested. The results of the reactions are presented in FIG. 11. In general, the enhancing effects of RecA protein depend on the RecA protein concentration, the protein/DNA ratio, the time of incubation, and the presence of the specific primer pairs at the appropriate concentrations (lane 7).

Figure 12:
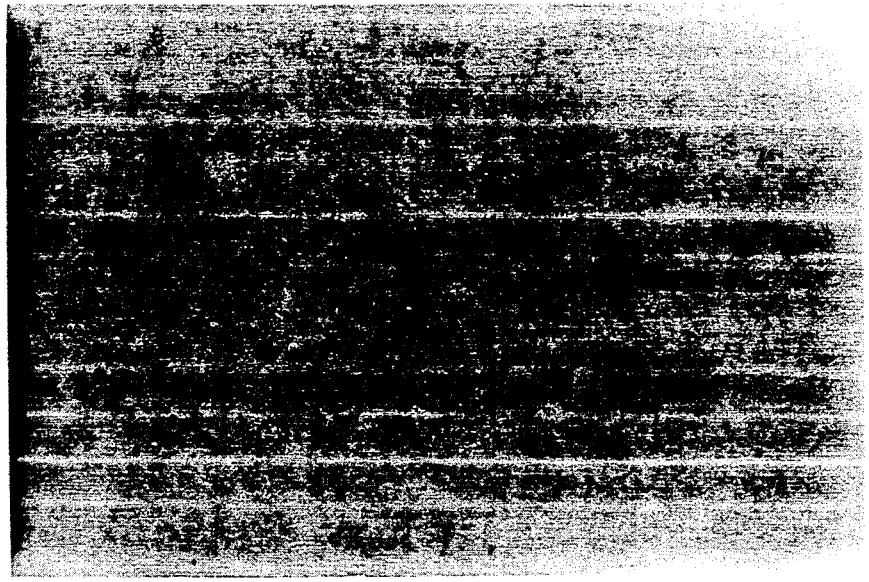
FIG. 12 shows results demonstrating that RecA+ enhances product specificity in single temperature amplification reactions.

Hybridization of a radiolabeled probe, specific for the 500 base pair λ template, to products of a Klenow single-temperature DNA amplification reaction catalyzed by RecA+ shows that RecA+ enhances true product synthesis (Example 9C). The data shown in FIG. 12 demonstrates that significant amplification of the 500 base pair template occurred only in the reaction which contained RecA+ and ATPγS and lacked SSB protein (Lane 3).

The method of the present invention permits the synthesis and amplification of native duplex, i.e. non-denatured, target DNA sequences, in solution, using RecA-catalyzed target hybridization with homologous oligonucleotide primer sequences. This hybridization reaction positions the primers for subsequent extension by DNA polymerases. The reaction is a two-step process and requires optimization of both steps of the reaction: (i) the primer hybridization; and, (ii) the primer extension.

Target DNA sequences can be obtained by a variety of methods and from many sources, for example: (i) the original target DNA sequence may be synthesized from a single-strand nucleic acid template, such as single-strand DNA or an RNA molecule, by standard procedures (Maniatis et al.); and, (ii) the original target sequence may be extracted from a cell or tissue source. The target DNA sequence can also be present in a homogeneous mixture, ie. predominantly composed of target sequences, or a heterogeneous mixture, ie. other sequences are present.

Initially, a primer complementary to the target sequence is reacted with the target DNA sequence under conditions which allow the RecA protein to catalyze the formation of joint-molecules between the primer and the target DNA. This reaction is carried out with native DNA substrates, i.e., the DNA strands are not heat-denatured. The multi-stranded structures, whose formation are catalyzed by RecA protein, are elongated using the Klenow fragment of DNA polymerase I in the presence of nucleotide triphosphates. RecA protein topologically prepares the hybrid DNA for DNA polymerase elongation.

In subsequent rounds of amplification, free primers complementary to the existing target DNA strands can either bind to an original strand or to the new strand. Once hybridized these complexes are then elongated using DNA polymerase as described above. The process is repeated and the target sequence is synthesized, thus amplified, many times. After a few rounds of amplification, the native target sequence can be detected using a labeled single-stranded DNA probe driven by mass action hybridization and/or by RecA protein/probe complexes in hybridization reactions catalyzed by the RecA protein. Alternatively, the reaction can be allowed to proceed for many rounds, providing an amplified product which can be visualized, for example, by electrophoretically resolving the separated reaction components on an agarose gel, followed by staining the separated DNA in the gel with ethidium bromide.

The advantage of using RecA+ and recA-803 proteins in DNA amplification and DNA synthetic reactions is that these proteins strongly facilitate efficient hybridization of the single-stranded DNA primer to target DNA sequences. Further, these proteins prepare the DNA primer-native-target complex topologically for extension. Because of the topological effects of RecA protein, cellular DNA polymerases, such as Klenow fragment of E. coli DNA polymerase I, can elongate the primer as the template strand is unwound. This reaction is simpler than amplification reactions which require heating to provide single strand templates and cooling to allow hybridization of the primers.

Accordingly, one major use of these RecA enhanced DNA syntheses is to amplify normal, light-damaged, or chemically-damaged DNA sequences using RecA-catalysis to properly position primers on their homologous targets for subsequent extension by DNA polymerases. Another advantage of the use of RecA protein-catalyzed DNA synthesis is the elimination of the requirement for multiple cycles of high-temperature thermal denaturation and renaturation (Saiki et al.).

A second important application, as discussed above, is the ability of RecA protein to topologically prepare DNA for DNA synthesis; in particular, DNA having conformations or secondary structures which are difficult to synthesize or amplify by traditional methods, such as heat denaturation.

A third important use of these RecA protein-catalyzed reactions takes advantage of the ability of the RecA protein/DNA primer complexes to efficiently find complementary sequences. The protein/primer complexes can, for example, be used as probes in diagnostic assays which depend on the identification of sequences in a sample based on their complementarity to the primer. The bound complex can then be stabilized and identified by a variety of methods, such as by antibodies directed against the recA-803 protein.

IV. Other Useful Proteins having the Activities of RecA Protein

In the present invention RecA protein refers to a family of RecA-like proteins all having essentially the same functions, particularly: (i) the protein's ability to properly position primers on their homologous targets for subsequent extension by DNA polymerases; (ii) the ability of RecA protein to topologically prepare DNA for DNA synthesis; and, (iii) the ability of RecA protein/DNA primer complexes to efficiently find and bind to complementary sequences. The best characterized RecA protein is from E. coli; in addition to the wild-type protein a number of mutant recA proteins have been identified (eg. recA-803). Further, many organisms have such RecA-like proteins (see below).

Another application of RecA protein catalyzed DNA synthesis is use in enhancing DNA polymerase amplification reactions at a constant elevated temperature using a heat-stable DNA polymerase. Heat-stable DNA polymerases have been isolated from a variety of sources, including: Thermus aquaticus (U.S. Biochemicals), Bacillus stearothermophilus, Sulpholubus, or Pyrodictium. Generally the activities of these enzymes are heat-stable up to about 95° C. A system such as this may allow amplification of DNA sequences having strong inhibitory structures or DNA sequences known to produce artifacts (McConlogue et al; Shuldiner et al.). E. coli RecA protein has a half-life of minutes at 52° C. and, accordingly, is too heat-sensitive for use at elevated temperatures; accordingly, a heat-stable RecA protein is required. A heat-stable RecA protein needs to retain its activity over essentially the same temperature range as the DNA polymerase with which it is being used (eg. up to about 95° C.).

In experiments performed in support of the present invention, the RecA protein from Thermus aquaticus has been identified and the gene encoding it cloned. Southern blot analysis of Thermus aquaticus genomic DNA was performed using the Aquaspirillum magnetotacticum RecA gene as a probe (Example 10). The Aquaspirillum magnetotacticum gene is unusually G-C rich and is likely a better match for the T. aquaticus RecA gene than the E. coli RecA gene. Single DNA bands were identified, by hybridization with the probe, in each of the following digests: 12–15 kb, BamHI; 5 kb, HindIII; and 1.5 kb, SstI.

To clone the T. aquaticus RecA gene, genomic DNA was purified from T. aquaticus, cut with the restriction endonuclease BamHI (Maniatis et al.), and then cloned into the EMBL Lambda cloning system (Promega). The large BamHI fragment (15kb) containing the T. aquaticus RecA gene from T. aquaticus was isolated from a phage DNA-containing clone which strongly hybridized to the probe under stringent conditions of hybridization washing. The gene is being subcloned into M13 vectors for complete sequencing. The gene is also being subcloned into Protoclone® lambda gtII vectors (Promega) for expression and identification of the RecA protein.

The ability of the T. aquaticus RecA protein to improve the length of the target and the final yield of the products in DNA amplification reactions is tested as described above for RecA proteins. In particular, templates having significant secondary structures are used as targets, such as human tRNA genes and the cluster of 21 tRNA genes found in a 2.5-kbp fragment of DNA from Bacillus subtilis (Green et al.).

The following examples illustrate, but in no way are intended to limit, the present invention.

Materials and Methods

DNAs and Enzymes

Synthetic polymers, including poly-[d(C-G)] and poly[d(br$^5$C-G)], were synthesized enzymatically with DNA polymerase from poly-[d(I-C)] templates (Pharmacia) and characterized as described previously (Zarling et. al., 1984a; 1984b; Zarling et al. 1990). Poly-[d(C-A)•(G-T)] was purchased from Pharmacia-P.L. Polynucleotides were sonicated to an average size of 550 base pairs (bp) as determined by agarose gel electrophoresis to generate oligonucleotides. Polynucleotide end-labeling was as described by Silberklang et. al. Restriction endonucleases were obtained from a variety of commercial sources (eg., New England Biolabs, and Boehringer Mannheim.

Purified wild-type RecA+ protein and restriction endonucleases were purchased from Pharmacia. RecA+ protein was stored at −70° C. in 20 mM Tris-HCl (pH=7.5), 0.1 mM EDTA, 0.1 mM dithiothreitol (DTT), in a final concentration of 50% (v/v) glycerol. M13mp18 DNA and ATP-γ-S were obtained from Boehringer Mannheim.

Agarose Gel Electrophoresis of Protein-DNA Complexes

Reactions were terminated by the addition of TBE buffer (90 mM Tris-HCl, 90 mM boric acid, 2.8 mM EDTA, pH=8) containing 0.25% bromphenol blue and 0.25% xylene cyanol all in 50% glycerol (v/v).

All samples were analyzed on 0.7% agarose gels routinely run in 1×Tris-borate-EDTA buffer (Maniatis et. al.). When the samples were protein/DNA complexes, agarose gels were electrophoresed at 4° C. for approximately 2-3 hours at 90 volts. DNA bands were visualized by staining the gel in 4 μg/ml ethidium bromide, destaining the gel in distilled water, and then photographing the gel using an ultra-violet light source.

Source of the DNA Primers

Primers were either purchased (eg., the primers in Table 1 are obtained from Cetus Perkin-Elmer) or prepared using commercially available automated oligonucleotide synthesizers. Alternatively, custom designed synthetic primers may be purchased, for example, from Synthetic Genetics (San Diego, CA).

EXAMPLE 1

Comparison of RecA-803 and RecA+ wild-type proteins Binding Efficiencies to DNA substrates This example describes the results of DNA binding reactions comparing the activities of RecA+ and recA-803 proteins.

Reactions were assembled in a volume of 0.01 ml containing: 10 mM Tris acetate buffer (pH =7.5 at 37° C.); 2 mM magnesium acetate; 1 mM dithiothreitol; 50 mM sodium acetate; 5% glycerol (added as 10×buffer); 1.6 mM ATP-γ-S; 0.05 μg phiX174 as circular virion DNA; and either 34.3 μM (FIG. 1, lanes 2, 5, and 6) or 17.1 μM (FIG. 1, lanes 3, 4, 7 and 8) of RecA+ or recA-803 proteins. The reaction mixtures were equilibrated for 10 minutes at 37° C. The concentration of magnesium was then increased to a final concentration of 12 mM by addition of 0.2 M magnesium acetate. 0.4 μg of XhoI digested phiX174 linear doublestranded DNA (form II DNA) and an appropriate volume of 10× buffer was then added to the mixture resulting in a final reaction volume of 20 μl. After 30 minutes of incubation at 37° C., all reactions were divided into 2 equal aliquots of which one was treated with proteinase K (10 mg/ml) for 15 minutes at 37° C. (lanes 2, 4, 6, and 8). The untreated samples corresponding to lanes 1 and 2 of FIG. 1 are not shown.

Comparison of lanes 3 and 7 (FIG. 1) clearly demonstrates that at equal protein concentrations RecA+ protein binds less double-stranded target DNA than recA-803 protein.

EXAMPLE 2

Comparison of the ATPase Activities of RecA+ and RecA-803 and Their Abilities to Catalyze Strand-transfer Reactions This example describes the results of ATPase and strand-transfer reactions comparing the activities of RecA+ and recA-803 proteins.

A. ATPase Activity Reactions

The ATPase activities of equal concentrations of RecA+ and recA-803 were compared. Reactions were carried out in a total volume of 18 μl of buffer containing 35 mM Tris-HCl (pH=7.5), 6.7 mM MgCl$_2$, 2 mM dithiothrietol, 100 μg/ml bovine serum albumin (BSA), 1.4 mM ATP, 0.002 μM [γ-$^{32}$-ATP. To these reaction mixtures RecA or RecA803 protein was added in the presence or absence of 50 μM single-stranded phiX174 phage DNA.

The reactions were incubated at 37° C. for 30 minutes in 0.6 ml microcentrifuge tubes. The reactions were terminated by chilling to 0° C. followed by the addition of 12 μl of 25 mM EDTA containing 3 mM each of unlabelled ATP, ADP and AMP as carrier. A 10 μl aliquot of each reaction was then spotted onto plastic-backed TLC sheets of PEI-cellulose F (Pharmacia) and the TLC sheets developed in a solvent containing 0.5 M LiCl and 0.25 M formic acid. Radioactive products were visualized by autoradiography. The areas corresponding to the liberated inorganic phosphate were scraped off of the TLC sheets and counted in a scintillation counter. The percent of hydrolysis was calculated by dividing the cpm of the product by the total cpm of the 10 μl sample.

FIG. 2A shows the results of the above reactions. Neither recA-803 (open diamonds) nor RecA+ (closed squares) have significant ATPase activity in the absence of DNA. However, RecA-803 protein (closed diamonds), in the presence of DNA, has superior ATPase activity when compared with RecA+ protein (open squares).

B. Strand-transfer Reactions

Reactions were assembled in a volume of 0.01 ml as in Example 1 with the following exceptions: 0.3 μg phiX174 single-stranded circular virion DNA was used instead of 0.05 μg; and, 34.3 μM of RecA+ or recA-803 proteins were used in all reactions.

After 30 minutes of incubation at 37° C., the reactions were divided in half and SDS was added to a final concentration of 0.5% to one-half of each sample. Gel loading dye (50% glycerol, 50% TEB, 0.25% bromphenol blue, 0.25% xylene cyanol; Maniatis et al.) was added to all the samples. The samples were electrophoresed for 3 hours at 7.6 V/cm in a standard 0.7% agarose gel, prepared as described above. DNA bands were visualized by staining with ethidium bromide.

The reactions in lanes 3, 4, 5, and 6 (FIG. 2B) contained RecA+ protein, whereas lanes 7 and 8 (FIG. 2B) contained recA-803 protein. Lanes 1 and 2 contained no RecA+ protein. Lanes 3, 6, and 8, were samples treated with SDS. The two bright bands in lane 1 correspond to the substrates of the reaction. Complete strand-transfer results in the formation of double-stranded nicked circular DNA (Form II); strand-transfer products are indicated by the arrow in FIG. 2B.

EXAMPLE 3

Increased Binding of RecA+ Protein to oligo-[d(br$^5$C-G)]and to N-acetoxy-N-2-acetylaminofluorene Modified DNA This example describes the results of RecA+ protein/double-stranded DNA binding assays which indicate the increased ability of the RecA+ protein to bind to light-damaged DNA, chemically-damaged DNA or DNA having the Z-conformation.

A. Preparation of Adducted DNA

N-acetoxy-N-2-acetylaminofluorene (obtained from Dr. Frederick Beland, National Center for Toxicological Research, Jefferson, Arizona) was stored at −20° C. Adduction reactions were performed in a total reaction volume of 50 μl and contained the following reagents: 2.5 μg of DNA (either oligo-[d(br$^5$C-G)] or oligo-[d(C-G)]); 0 to 200 mM N-acetoxy-N-2-acetylamino-fluorene (N-AcO-AAF); 50 mM NaCl; and, 5 mM Tris-HCl, pH=7.5. The reactions were performed for 10 minutes at 25° C. in the dark. Unbound N-AcO-AAF was removed by extraction with 20 volumes of ice-cold anhydrous diethyl ether. The adducted DNA was then ethanol precipitated and extensively dialyzed against 10 mM Tris-HCl, 1 mM EDTA, pH=7.5. The extent of modification of each reaction was determined from the $A_{305}/A_{260}$ ratio as described by Fuchs et. al. (1972), using an extinction coefficient of $\epsilon = 18,000$ for N-AcO-AAF. DNA having 5–20% adduction of N-AcO-AAF was used in subsequent reactions.

B. RecA+ protein Binding Assays

The DNA substrates used in the binding assays were endlabelled using adenosine [γ-P$^{32}$] triphosphate (New England Nuclear) by the method of Silberklang et. al. The binding reactions had a total volume of 50 μl and contained the following: 0.57 μM of oligo-[d(br$^5$C-G)] or oligo-[d(C-G)]; 0.33 μM RecA+ protein; TEA buffer (25 mM triethanolamine, pH=7.5, 1.0 mM dithiothreitol, and 5.0 mM MgCl$_2$); and 20 μM ATP-γ-S. The reactions were initiated by the addition of the RecA+ protein at 37° C. and incubated for the time periods specified in FIG. 3.

All reactions were terminated by filtration on nitrocellulose membrane filters (Millipore, Millititer®-STHA09610), which were pre-wetted with double distilled water and primed with TEA buffer prior to sample filtration. Filters were washed 6 times with TEA buffer, dried under a heat lamp, and immersed in Aquasol-2 (DuPont, New England Nuclear). The radioactivity retained on each filter was measured using a liquid scintillation counter (Hewlett Packard Model 2000CA). Under these conditions the retention of protein-bound-DNA by the nitrocellulose was approximately 50% efficient.

FIG. 3 illustrates the results of the DNA binding assays. The symbols in FIG. 3 represent the following DNA substrates: open squares, oligo-[d(br$^5$C-G)]; closed squares, N-AcO-AAF adducted oligo-[d(br$^5$C-G)]; open triangles, oligo[d(C-G)]; closed triangles, N-AcO-AAF adducted oligo[d(C-G)].

FIG. 3 shows the increased binding of RecA+ protein to chemically modified (N-AcO-AAF adducted) DNA relative to unmodified DNA; further, the figure illustrates the increased binding of RecA+ protein to oligo-[d(br$^5$C-G)], having a Z-DNA conformation, relative to oligo[d(C-G)], having a B-DNA conformation.

EXAMPLE 4

Preferential binding of RecA+ protein to double-stranded oligo-[d(C-A)•d(G-T)] relative to either oligo[d(C-G)] or oligo-[d(br$^5$C-G)]

This example describes the results of DNA binding assays which demonstrate the preferential binding of RecA+ protein to certain double-stranded DNAs containing alternating sequences of purines and pyrimidines [e.g., (PuPyPuPyPuPyPuPy)$_n$].

Figure 4A:
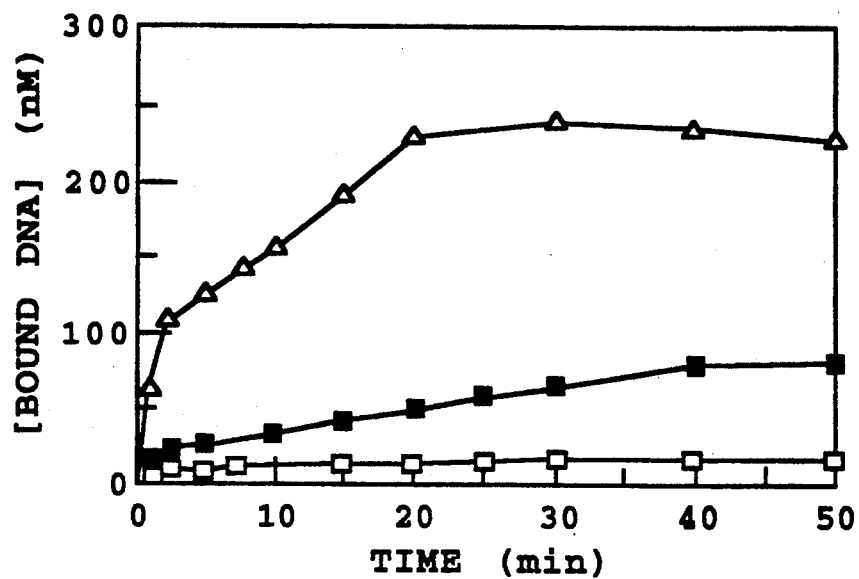

A. Constant RecA+ Protein/DNA Concentration (FIG. 4A)

The DNA binding reactions had a total volume of 50 μl and contained the following components: 0.35 μM RecA+ protein; 0.7 μM DNA (molecules) substrate; TEA buffer (see above); and 20 μM ATP-γ-S. The reactions were carried at 20° C. and terminated by filtration of the protein/DNA complexes on nitrocellulose filters (described in Example 3) at the time points illustrated in FIG. 4A.

B. Constant DNA Concentration with Increasing RecA+ Protein Concentration

The DNA binding reactions had a total volume of 50 μl and contained the following components: 0 to 5.0 μM RecA+ protein; 1.0 μM DNA substrate (molecules); TEA buffer (see above); and 20 μM ATP-γ-S. The reactions were carried at 20° C. for 20 minutes and terminated by filtration of the protein/DNA complexes on nitrocellulose filters (described in Example 3).

The DNA substrates used in the above reactions were as follows for FIGS. 4A and 4B: open squares, oligo-[d(C-G)]; closed squares, oligo-[d(br$^5$C-G)]; and, open triangles, oligo-[d(C-A)•d(G-T)].

Figure 4B:
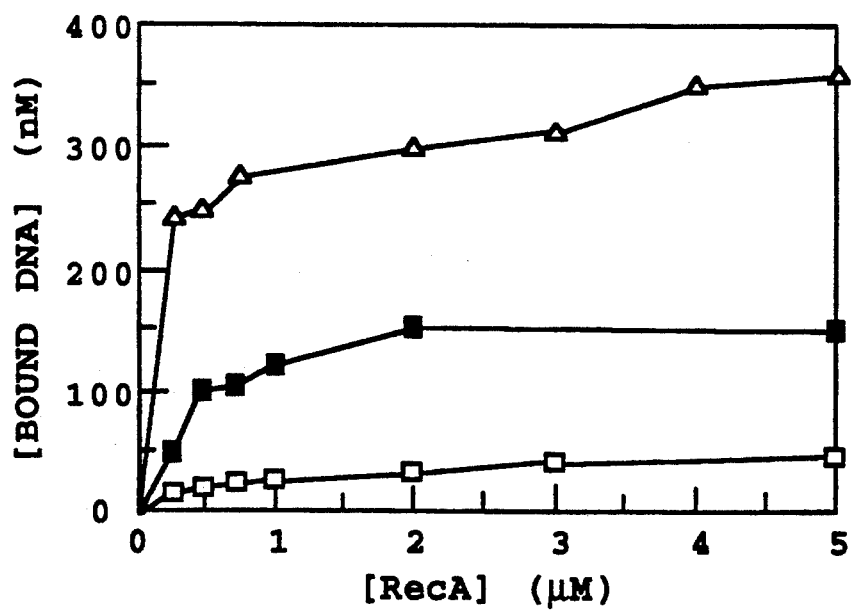

FIGS. 4A and 4B clearly illustrate the binding preference of RecA+ protein to the following sequences of alternating purines and pyrimidines, in decreasing order of preference: double stranded oligo-[d(C-A)•[d(G-T)], having the right-handed B-conformation; oligo-[d(br$^5$C-G)], having the left-handed Z-conformation; and, oligo-[d(C-G)] having the right-handed B-conformation.

EXAMPLE 5

RecA+ Protein Enhancement of DNA Synthesis on Single-Stranded Circular DNA Templates This example describes the results demonstrating an enhancing effect of RecA+ protein on bulk DNA synthesis from a single-stranded template.

The 24-mer primer [d(AGCGGATAACAATTT-CACACAGGA)] was coated with RecA+ and protein using ATP-γ-S. The coated primer was added to M13mp18 single-stranded DNA in a reaction mixture containing rATP; the RATP regenerating system PEP/PK (Boehringer Mannheim); dNTPs and [$^3$H]dGTP (New England Nuclear); E. coli single-strand binding (SSB) protein (U.S. Biochemical Corporation). The total reaction volume was 26.25 μl. These conditions were varied by the presence or absence of RecA+ protein and SSB protein (see FIG. 5). After 4 minutes at 37° C., 0.5 units of the Klenow large fragment of DNA polymerase I (New England Biolabs) was added.

Reactions were incubated at 37° C. and sampled at 5 minute intervals for 15 minutes. Reaction samples were collected by cold 5% Trichloroacetic acid precipitation of the $^3$H-labeled DNA and filtration on glass filters (Schleicher and Schuell, Inc.). The amount of [$^3$H]dGTP incorporated into newly synthesized high-molecular-weight DNA was determined by counting the glass filters in a toluene-based scintillation mix using a Packard P2000 liquid scintillation counter.

The results of the reactions are presented in FIG. 5. The components of the reactions were as follows: open circles, DNA polymerase I; closed circles, DNA polymerase I and SSB protein; open squares, DNA polymerase I and RecA+ protein; and, the closed squares, DNA polymerase I, RecA+ protein, and SSB protein.

The results illustrated in FIG. 5 show that the addition of RecA+ protein in the absence of SSB protein improves bulk DNA synthesis. Further, there appears to be a synergistic effect of SSB protein and RecA+ protein on DNA synthesis from a single-stranded circular template.

EXAMPLE 6

RecA-803 Protein Enhanced DNA Synthesis on Linear Double -Stranded DNA Templates This example describes the results demonstrating the enhancement of bulk DNA synthesis by RecA+-803 protein.

The double-stranded linear template for these reactions was plasmid pJC801-886, containing the coding sequences for the E. coli RecA gene, cut with restriction endonuclease SalI resulting in an 8 kilobase (kb) linear fragment.

The following RecA gene-specific primers were used: primer A [d(ATGCGACCCTTGTGTATC)]; and, primer B [d(GTGGTGGGTAGCAAACC)]. The primers were coated with RecA+ protein (3.0 μM), in 30 mM Tris-acetate, 60 mM sodium acetate, 10 mM Mg acetate, further containing the PEP/PK (Boehringher Mannheim) rATP regenerating system, for 5 minutes at 37° C.

The DNA synthesis reactions were performed in a total reaction volume of 32 μl. The reactions contained 0.5μg pJC801-886, 0.6 μM each of primers A and B, 30 mM Tris-acetate, pH=8.3, 60 mM Na acetate, 10 mM Mg acetate, the ATP regenerating system described in Example 5, dNTPs, and [α-$^{35}$S]dATP. Five units of Klenow DNA polymerase I were added. Reactions were incubated at 37° C. for 30 minutes and sampled at the time points indicated in FIG. 6. Reaction samples were collected by cold 5% Trichloroacetic acid precipitation of the $^{35}$S-labeled DNA and filtration on glass filters (Schleicher and Schuell, Inc.). The amount of [$^{35}$S]dATP incorporated into newly synthesized high-molecular-weight DNA was determined by counting the glass filters in a toluene-based scintillation mix using a Packard P2000 liquid scintillation counter.

The results illustrated in FIG. 6 (open squares, in the absence of recA-803 protein; and closed squares, in the presence of recA-803 protein) clearly demonstrate the enhancement of bulk DNA synthesis from a linear double-stranded template in the presence of recA-803 protein.

EXAMPLE 7

RecA+ Protein Enhanced DNA Synthesis on Native Linear Lambda DNA Templates

This example describes the results demonstrating the RecA+ protein enhancement of DNA synthesis from native lambda DNA templates using 25-mer primers.

A. Preparation of RecA+ Protein/Primer Complexes

The following primers were used for the DNA synthesis reactions:

TABLE 1

| Primer or Probe | Nucleotides | λ DNA Sequence |
|---|---|---|
| 1 PCR01-25 mer | 7131-7155 | (5')GATGAGTTCGTGTCCGTACAACTGG(3') |
| 2 PRC02-25 mer | 7606-7603 | (5')GGTTATCGAAATCAGCCACAGCGC(3') |
| 3 PRC01A-40 mer | 7131-7170 | (5')GATGAGTTCGTGTCCGTACAACTGGCG-TAATCATGGCCCT(3') |
| 4 PRCO2A-40 mer | 7591-7630 | (5')GGTTATCGAAATCAGCCACCAGCGCCTC-CCGTTATTGCATT(3') |

The primer sequences (Cetus-Perkin Elmer, Norwalk, CT) were derived from the lambda viral DNA sequence. The lambda viral genome is approximately 48.5 kb. The DNA segment targeted by the primers is 500 base pair (bp), including the primer sequences, which is about 1% of the total lambda genome.

RecA+ protein was bound to the single-stranded DNA primers under the following conditions: 0.66 μM RecA+ protein was incubated with 1 μM final concentration of each primer (2 μM total). The reaction mixture was incubated for 10 minutes at 22° C. RecA+ protein was effectively bound to the single-stranded primers under these conditions as evidenced by gel retardation of the primer/RecA+ protein complexes.

After the 10 minute incubation, the RecA-primer mixture was added to the reaction mixture (10 mM Tris-HCl, pH=7.5; 50 mM NaCl; 10 mM MgCl$_2$, 750 μM dNTPs final concentration, 10% DMSO final concentration). Next, 1 μM final concentration ATP-γ-S and 0.094 mM final concentration of SSB protein was added to the reaction, followed by the addition of 0.5 μg lambda viral genomic DNA (New England Biolabs).

B. DNA Synthesis is Enhanced by the Presence of RecA+ Protein

The above reaction mixtures were equilibrated at 37° C. for 3 minutes. DNA synthesis reactions were initiated by the addition of 1 unit Klenow DNA polymerase I (Klenow). The reactions were maintained at 37° C. Following the initial addition of Klenow, the reactions were supplemented with 1 unit of Klenow at 10 minute intervals seven times over the 80-minute course of the reaction.

The following specific reaction conditions were used to examine the effect of the addition of the RecA+ protein on the DNA synthesis reactions (FIG. 7): (a) lane 1, eight successive additions of 0.66 μM RecA+ protein and 0.094 mM SSB protein at 10 minute intervals; (b) lane 2, eight successive additions of 0.66 μM RecA+ protein, 0.094 mM SSB protein, and 1 mM ATP-γ-S at 10 minute intervals; (c) lane 3, only the initial addition of RecA+ protein complexed to the primers followed by eight successive additions of ATP-γ-S and SSB protein; and, (d) lane 4, a control reaction from which RecA+ protein, SSB protein, and ATP-γ-S were omitted. Lanes 5 and 6 contain lambda DNA (0.5μg) and a set of 1 kb DNA molecular weight markers (BRL), respectively.

The products of the reactions were separated by electrophoresis in a 0.7% agarose gel and the DNA bands visualized by staining with ethidium bromide. The results are illustrated in FIG. 7.

FIG. 7 shows that lambda DNA synthesis was enhanced by the inclusion of RecA+ protein. The enhancement is indicated by an increased concentration of DNA products in the lanes containing RecA+ protein; as evidenced by enhanced ethidium bromide staining.

C. Enhancement of DNA Synthesis by RecA+ Protein is Independent of Single-Strand Binding Protein The reaction conditions were as described in section A above. The reaction mixtures were equilibrated at 37° C. for 3 minutes. DNA synthesis reactions were initiated by the addition of 1 unit Klenow DNA polymerase I (Klenow). The reactions were maintained at 37° C. Following the initial addition of Klenow, the reactions were supplemented with 1 unit of Klenow at 10 minute intervals over the 80 minute course of the reaction. Each reaction received 8 units of Klenow including the initial addition of 1 unit.

The following specific reaction conditions were used to test the effect of E. coli single-strand binding (SSB) protein on DNA synthesis in the presence of RecA+ protein. The first reaction (lane 1, FIG. 8) contained no SSB protein. The second reaction (lane 2, FIG. 8) contained 0.094 $\mu$M SSB protein added to the reaction after the addition of the RecA+ protein primer. The third reaction was a control reaction which contained neither RecA+ protein nor SSB protein (lane 3, FIG. 8). All the reactions contained 1 mM ATP-$\gamma$-S and were incubated at 37° C. for 80 minutes.

At the end of 80 minutes 2.5 $\mu$l of Proteinase K (50 $\mu$g/$\mu$l) were added to the reactions and the mixtures held at 37° C. for 15 minutes. The DNA molecules were then separated by agarose gel electrophoresis.

The results of the above reactions are shown in FIG. 8. The samples loaded in each lane were described above. Lane 4 contained a standard 1 kb molecular weight ladder (BRL). The appearance of large molecular weight products in lanes 1 and 2 clearly demonstrates that the DNA synthesis reaction is not dependent on the presence of SSB protein. Lane 3 does, however, indicate the reliance of the reaction on the presence of RecA+ protein.

EXAMPLE 8

RecA+ protein Enhances Primer Dependent DNA Synthesis at 37° C.

This example describes the results illustrating the dependence of the DNA synthesis reactions on the presence of both RecA+ protein and the lambda-specific primers.

The reaction conditions were essentially as described in Example 7A with the following exceptions. The first reaction contained RecA+ protein, but the primers were omitted (lane 1, FIG. 9). The second reaction contained primers but no RecA+ protein (lane 2, FIG. 9). The third reaction contained both RecA+ protein and the primers (lane 3, FIG. 9).

The reaction mixtures were equilibrated at 37° C. for 3 minutes. DNA synthesis reactions were initiated by the addition of 1 unit of exonuclease-free E. coli DNA polymerase I (a double mutant of the large Klenow fragment, the enzyme is available from U.S. Biochemicals). The reactions were maintained at 37° C. Following the initial addition of polymerase, the reactions were each supplemented with additional units of Klenow at ten minute intervals. Reactions were incubated at 37° C. for a total of 72 hours. The 28$\mu$l samples were treated with proteinase K, as above, before being loaded for electrophoretic separation.

As can be seen from lane 3, FIG. 9, DNA synthesis occurs only in the presence of RecA+protein and the lambda-specific primers.

EXAMPLE 9

RecA+ Facilitated DNA Amplification at 37° C.

The results in this example illustrate the enhancement of DNA synthesis from a 500 bp lambda target sequence by RecA+protein.

A. The Effect of SSB protein

The reaction conditions were essentially as described in Example 7A with the following exceptions. All the reactions contained 0.5 $\mu$g of a 500 bp template, corresponding to nucleotides 7131-7630 of the lambda genome which had been purified from the product of a T. aquaticus DNA polymerase I-catalyzed thermal amplification using lambda DNA template (Mullis), replacing the native lambda genomic DNA. The first two reactions contained no RecA+ protein (lanes 2 and 3, FIG. 10). The third reaction contained 0.66 $\mu$M final concentration RecA+ protein and no SSB protein (lane 4, FIG. 10). The fourth reaction contained 0.66 $\mu$M final concentration RecA+ protein and 0.094 $\mu$M final concentration SSB protein (lane 5, FIG. 10).

The reaction mixtures were equilibrated at 37° C. for 3 minutes. DNA synthesis reactions were initiated by the addition of 1 unit of exonuclease-free E. coli DNA polymerase I (U.S. Biochemicals). The reactions were maintained at 37° C. Following the initial addition of polymerase, the reactions were supplemented with 1 unit of Klenow each 10 minutes for an additional 70 minutes. The time course of the reaction was 17.5 hours. Samples were treated with proteinase K, as above, before being loaded for electrophoretic separation.

Figure 10:
FIGS. 10 and 11 show results demonstrating RecA+ protein catalyzed single temperature DNA amplification reactions.

As can be seen from FIG. 10, there is no DNA synthesis in the absence of RecA+ protein (lanes 2 and 3). The 500 bp template was loaded in lane 1 as a standard. The synthesis performed in the presence of RecA+ protein (lane 4) shows a product band of comparable size to the 500 bp template. However, the synthesis performed in the presence of RecA+protein and SSB protein appears to generate newly synthesized products smaller than the 500 bp template (lane 5).

B. The Effects on DNA Synthesis of Each Component of the Reaction Mixture

The reaction conditions were as described above in this example. The following chart summarizes the reaction conditions used.

TABLE 2

| Reaction Lane | RecA+ | SSB Protein | ATP$\gamma$S Cofactor | 40-mer Primers | 25-mer Primers | 500 b-p Template | Klenow |
|---|---|---|---|---|---|---|---|
| 1 | + | + | + | + | − | + | + |
| 2 | + | + | + | − | − | + | + |
| 3 | + | + | − | + | − | + | + |
| 4 | + | − | + | + | − | + | − |
| 5 | + | − | + | + | − | − | + |
| 6 | − | − | + | − | + | + | + |
| 7 | + | − | + | − | + | + | + |
| 8 | + | + | + | − | + | + | + |
| 9 | − | − | + | + | − | + | + |
| 10 | − | + | + | + | − | + | − |

The concentrations of these components in the reaction mix were as follows: 0.66 $\mu$M RecA+ protein;

0.094 μM SSB protein; 1 μM ATP-γ-S; 2 μM 40-mer primers; 2 μM 25-mer primers; 0.5 μg 500 bp template; 1 unit/additions of 8 units total exonuclease-free DNA polymerase I. The reaction numbers correspond to the lane numbers shown in FIG. 11.

Figure 11:
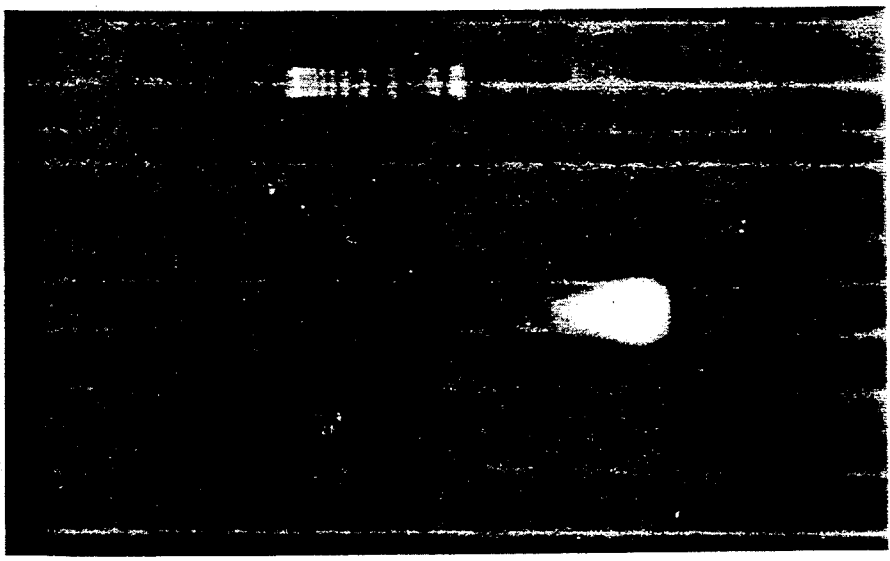

As can be seen from the results displayed in FIG. 11, DNA synthesis is most effectively enhanced under the reaction conditions given above for reaction 7; the presence of RecA+ protein and ATP-γ-S. Reaction 8 contained the same components as reaction 7 with the exception that SSB protein was also included. Comparison of lanes 8 and 7 illustrates that the presence of SSB protein does not enhance the effects of RecA+ protein and ATP-γ-S on DNA synthesis from a double-strand template.

C. RecA+ Enhances Specific Amplification In Single Temperature Reactions

All the reactions contained 0.5 μg of a 500 bp template, corresponding to nucleotides 7131-7630 of the lambda genome which had been purified from the product of a *T. aquaticus* DNA polymerase I-catalyzed thermal amplification using lambda DNA template (Mullis), replacing the native lambda genomic DNA. The reaction conditions were essentially as described in Example 7A with the following exceptions: reaction 1 contained ATP-γ-S and lacked RecA+ and SSB protein (lanes 1, FIG. 12); reaction 2 contained ATP-γ-S and SSB protein and lacked RecA+ protein (lane 2, FIG. 12); reaction 3 contained ATP-γ-S and RecA+ and lacked SSB protein (lane 3, FIG. 12); and, reaction 4 contained all of the reaction components (lane 4, FIG. 12).

Single-temperature DNA synthesis reactions were performed essentially as described above in Example 7A. After 72 hours of incubation at 37° C., 16 μl aliquots from each reaction were treated with protinease K (100 μg/aliquot) for 15 minutes at 37° C. and then loaded onto a 0.7% agarose gel. After electrophoretic separation the DNA fragments were transferred by standard protocols (Maniatis et al.) onto hybridization transfer membrane (Hybond-N, Amersham). The DNA was UV cross-linked (Stratalinker, Stratagene) to the membrane. The UV-treated transfer membrane was hybridized with 32p-end-labelled probe PCR03A: PCR03A (nucleotides 7351 through 7390 of the native lambda genome) is a 40-mer corresponding to an internal DNA sequence of the 500 base pair lambda template used in the above amplification reaction. The membrane was then autoradiographed.

Hybridization of specific radiolabeled probe to products of a Klenow single temperature RecA+ catalyzed amplification reaction shows that RecA+ enhanced true product synthesis. The autoradiograph (FIG. 12) clearly demonstrates that significant amplification of 500 base pair product occurred only in the reaction which contained RecA+ and ATP-γ-S and lacked SSB protein (Lane 3).

EXAMPLE 10

Identification and Cloning of the Thermus aquaticus RecA Gene

This example describes the identification of the *T. aquaticus* RecA gene by Southern hybridization analysis and the subsequent cloning of the gene.

Genomic DNA was purified from *T. aquaticus* and was digested with the following restriction enzymes: BamHI, HindIII, and SstI. The digested DNA was loaded onto a 0.8% agarose gel, electrophoresed, and the DNA fragments transferred to a nitrocellulose membrane (Maniatis et al.). As a probe, the RecA gene from *Aquaspirillum magnetotacticum*, which has a 61.6% homology to the RecA gene of *E. coli* (A. Berson, M. Peters, and N. Waleh, all of SRI International, personal communication) was used; *A. magnetotacticum* has codon usage similar to *T. aquaticus*. The probe consisted of the sequence shown in FIG. 13 plus an additional 800 bases of uncharacterized genomic *A. magnetotacticum* DNA. The probe was radioactively labeled using nick-translation (Bethesda Research Laboratories).

Southern hybridization was performed using standard techniques (Maniatis et al., 1987) at 42° C. in 20% formamide. The hybrids were washed under stringent conditions at 55° C. in 0.1 ×SSC and 0.1% SDS. The autoradiogram showed only a single band for each restriction digest. The DNA bands that hybridized to the probe were 12-15 kb, 5 kb and 1.5 kb for the Bam HI, Hind III, and Sst I digests, respectively.

To clone this RecA gene, the above-described BamHI T. aquaticus genomic DNA was cloned into the EMBL Lambda cloning system (Promega). The resulting phage vectors were plated and plaques generated. The phage DNA was transferred to nitrocellulose filters (plaque lifting, Maniatis et al.). As described above the *Aquaspirillum magnetotacticum* recA gene (FIG. 13) was used as a probe for the *Thermus aquaticus* recA gene. The nitrocellose filters were hybridized with the labeled probe. From a phage DNA-containing clone which strongly hybridized to the probe under stringent conditions of hybridization washing, a large BamHI fragment (15kb) containing the *T. aquaticus* RecA gene was isolated.

It is claimed:

1. A method of achieving synthesis and amplification of a double-stranded DNA target sequence having first and second complementary strands, each strand with 5' and 3' ends, comprising:
   (a) complexing a primer complementary to a 5' end region of the first strand and a primer complementary to a 5' end region of the second strand with heat-stable RecA protein in the presence of ATP-γ-S;
   (b) reacting the complexed primers in a reaction mixture also containing the target sequence, all four dNTPs, and a heatstable polymerase, said reacting performed above about 50° C. and below the temperature required for thermal dissociation of the target strands and their respective primers, and said reacting continued until a desired degree of amplification of the target sequence is achieved.

2. The method of claim 1, wherein the heat-stable RecA protein is the RecA protein of *Thermus aquaticus*.

3. The method of claim 1, wherein the heat-stable DNA polymerase is DNA polymerase I of *Thermus aquaticus*.

4. The method of claim 3, wherein the heat-stable RecA protein is the RecA protein of *Thermus aquaticus*.

* * * * *